United States Patent
Dholakia et al.

(10) Patent No.: US 8,922,767 B2
(45) Date of Patent: Dec. 30, 2014

(54) RAMAN SPECTROSCOPY

(75) Inventors: Kishan Dholakia, Fife (GB); Phillip Ronald Thomas Jess, Fife (GB); Michael Mazilu, Fife (GB)

(73) Assignee: The University Court of the University of St Andrews, St Andrews (GB)

(*) Notice: Subject to any disclaimer, the term of this patent is extended or adjusted under 35 U.S.C. 154(b) by 764 days.

(21) Appl. No.: 12/303,526

(22) PCT Filed: Jun. 8, 2007

(86) PCT No.: PCT/GB2007/002121
§ 371 (c)(1),
(2), (4) Date: Apr. 28, 2009

(87) PCT Pub. No.: WO2007/141539
PCT Pub. Date: Dec. 13, 2007

(65) Prior Publication Data
US 2010/0014078 A1    Jan. 21, 2010

(30) Foreign Application Priority Data

Jun. 8, 2006 (GB) .................................. 0611289.0

(51) Int. Cl.
*G01J 3/44* (2006.01)
*G01N 21/65* (2006.01)
*G01J 3/433* (2006.01)
*G01J 3/28* (2006.01)
*B01L 3/00* (2006.01)

(52) U.S. Cl.
CPC ................. *G01J 3/433* (2013.01); *G01N 21/65* (2013.01); *G01N 2021/651* (2013.01); *G01J 3/44* (2013.01); *B01L 3/5027* (2013.01); *G01N 2021/656* (2013.01); *G01J 3/28* (2013.01)
USPC ........................................................ 356/301

(58) Field of Classification Search
USPC ........................................................ 356/301
See application file for complete search history.

(56) References Cited

U.S. PATENT DOCUMENTS

| | | | | |
|---|---|---|---|---|
| 5,498,875 | A * | 3/1996 | Obremski et al. | 356/301 |
| 6,044,285 | A | 3/2000 | Chaiken et al. | |
| 7,515,269 | B1 * | 4/2009 | Alexander et al. | 356/445 |
| 2005/0105084 | A1 | 5/2005 | Wang et al. | |
| 2005/0221333 | A1 | 10/2005 | Sundararajan et al. | |
| 2005/0254047 | A1 * | 11/2005 | Brady et al. | 356/301 |
| 2006/0061761 | A1 | 3/2006 | Li et al. | |
| 2010/0241357 | A1 * | 9/2010 | Chan et al. | 356/301 |

FOREIGN PATENT DOCUMENTS

WO    WO-2005/029139    3/2005

OTHER PUBLICATIONS

Constable et al., "Demonstration of a fiber-optical light-force trap", Nov. 1, 1993, Optic Letters, vol. 18, No. 21, pp. 1867-1869.*
Ramser et al., "Resonance Raman spectroscopy of optically trapped functional erythrocytes", Jun. 2004, Journal of Biomedical Optics, vol. 9, No. 3, pp. 593-600.*

(Continued)

*Primary Examiner* — Kara E Geisel
(74) *Attorney, Agent, or Firm* — W. Kevin Ransom; Moore & Van Allen PLLC

(57) ABSTRACT

A micro-fluidic system comprising means for optically trapping a particle and a Raman excitation source for causing Raman scatter from the particle while it is in the optical trap.

20 Claims, 16 Drawing Sheets

(56) References Cited

OTHER PUBLICATIONS

Levin, K. H. et al: "Wavelength-modulation Raman Spectroscopy", Applied Physics Letters, American Institute of Physics, vol. 33, No. 9, Nov. 1, 1978, pp. 817-819.

Ashkin, A. et al: "Observation of a Single-beam Gradient Force Optical Trap for Dielectric Particles", Optics Letters, OSA, Optical Society of America, vol. 11, No. 5, May 1986, pp. 288-290.

Ramser, K. et al: "A Microfluidic System Enabling Raman Measurements of the Oxygenation Cycle in Single Optically Trapped Red Blood Cells", Lab on a Chip, No. 5, Feb. 21, 2005, pp. 431-436, XP002451679.

Anquetil, P. A. et al: "Laser Raman Spectroscopic Analysis of Polymorphic Forms in Microliter Fluid Volumes", The Journal of Pharmaceutical Sciences, vol. 92, No. 1, Jan. 1, 2003, pp. 149-160, XP002451680.

Berger, A. J.: "Novel Near-Infrared Raman Spectroscopy of Biological Fluids", Conference Proceedings—Lasers and Electro-Optics Society Annual Meeting—LEOS, Nov. 14-15, 2001, pp. 261-262, XP002452310.

Xie, Changan et al: "Near-infrared Raman Spectroscopy of Single Optically Trapped Biological Cells", Optics Letters, OSA, Optical Society of America, Washington, DC, US, vol. 27, No. 4, Feb. 15, 2002, pp. 249-251, XP002260524.

Shreve, Andrew P. et al: "Effective Rejection of Fluorescence Interference in Raman Spectroscopy Using a Shifted Excitation Difference Technique", Applied Spectroscopy, the Society for Applied Spectroscopy, Baltimore, US., vol. 46, No. 4, Apr. 1, 1992, pp. 707-711, XP000264023.

International Search for PCT/GB2007/002121, dated Sep. 25, 2007.

* cited by examiner

RAMAN SPECTROSCOPY

FIELD OF THE INVENTION

The present invention relates to Raman spectroscopy. In particular, the invention relates to the use of Raman spectroscopy for investigating biological material, for example, single cells.

BACKGROUND OF THE INVENTION

Raman spectroscopy is a powerful technique that relies on collection of inelastically scattered laser light from a sample. This light exhibits a frequency shift that reflects the energy of specific molecular vibrations within the sample of interest. Hence, it can provide a detailed chemical composition of the sample, i.e. a chemical fingerprint. The technique has wide potential in biomedical science as it may be applied to samples over a wide size range from single cells through to intact tissue.

One of the major challenges of Raman spectroscopy is the inherently weak nature of the signal. In addition, a Raman signal may be obtained from the local environment surrounding the sample, typically making it difficult to discern the molecular signatures of interest. Thus, considerable effort has focussed on enhancing the ratio of signal to background noise. By increasing the acquisition time to several minutes, the signal to noise ratio can be improved. However, in some environments, long acquisition times can cause damage due to extended irradiation by the excitation laser and the mechanism required to hold the particles under investigation in the measurement position. These are particular problems when investigating live cells or tissue samples.

Some solutions to the problems with conventional Raman spectroscopy have been proposed. Many of these involve the inclusion of additional material, for example nano-particles, in the samples that are being investigated. However, this is not ideal for the investigation of whole cells as the precise positional control of the foreign particles is difficult. Additionally, the enhancement achieved with the use of foreign particles is confined to the immediate surface of the particles (~10 nm) making the measurement of the overall Raman signal impossible. One technique that does not require the addition of foreign particles uses wavelength modulation. This is described in the article "Wavelength-Modulation Raman Spectroscopy" by Levin et al, Appl. Phys Letter 33(39), 1 Nov. 1978. This technique increases the sensitivity of a Raman spectroscopic system by modulating the wavelength of the excitation light, and then using this to distinguish the sample's Raman response from background radiation and/or noise. The system described uses a tunable dye laser and single channel slowly scanning detection. A problem with this is that the scan takes about 50 minutes for the whole spectra. Additionally the method relies on very large, expensive optics and is inappropriate for many practical applications, in particular the investigation of single cells.

One of the most promising areas of application for Raman spectroscopy is in the discrimination between sets of biomedical samples e.g. cancer diagnostics. Here, it is advantageous to have short acquisition times, especially if a live patient rather than a retrieved sample is being studied. It is also important to reduce the impact of fluorescence, as this has a high patient to patient and even cell to cell variability that can heavily reduce the performance of any subsequent diagnostic models. One of the most widely used tools for discriminating between the Raman spectra acquired from sets of biomedical samples is Principal Component Analysis (PCA).

Principal components analysis (PCA) is a statistical technique used to change the representation of a multidimensional data set. A new representation or coordinate system is constructed such that the variance of the data sets is biggest for the first coordinate component of the new representation. This is then called the first principal component. The second biggest variation lies the on the second coordinate of the new representation, and so on. Finally, the data set dimension is reduced by retaining only the first few principal components that account for most of the variance of the original data set. It is these low-order components that often contain the "most important" aspects of the data set. Using PCA to examine Raman spectra from sets of biomedical samples allows combinations of Raman peak fluctuations to be found that can then be used to discriminate between the Raman spectra from the sets of biomedical samples.

SUMMARY OF THE INVENTION

According to the present invention, there is provided a micro-fluidic system comprising means for optically trapping a particle and means for obtaining a Raman spectrum from the particle whilst it is in the optical trap.

Typically, the means for forming an optical trap comprise a dual beam arrangement, in which counter propagating optical beams are used to hold the particle. Because the trapping beams are divergent, this arrangement reduces the chance of damage to the particle under investigation. This is particularly advantageous when the particle is a cell. The laser for exciting the Raman scatter may be placed orthogonal to the trapping beams.

Means may be provided for modulating the Raman excitation signal. The modulation means may be operable to encode information onto one or more parameters of the excitation signal. The modulation means may be operable to modulate one or more of the excitation laser driving current; intra-cavity or external cavity grating position and/or orientation; change of the cavity length, using, for example mechanical or opto-electric means; polarisation variation; excitation mode variation and variation of the optical properties of any intra-cavity or external cavity non-linear optical elements.

Any suitable laser can be used to form the Raman excitation signal, although a laser diode in a Littrow or Littman-Metcalf configuration is preferred. Alternatively, two or more laser sources may be combined where each has a different wavelength. In this case, each of the sources can be independently switched and its intensity varied to achieve an efficient modulated multi wavelength excitation.

The Raman excitation can also be provided by a broadband light source such as mode-locked pulsed lasers, delivering 100 fs pulses, for example, or other sources such as a white light source. These sources can have their spectral phase/chirp specially engineered and/or modulated. This can be achieved, for example, by passing the pulse through a Fabry-Perot resonator giving a periodic spectral phase modulation. More complex spectral phase/chirp modulation can be obtained through the use of a Spatial Light Modulator (SLM) in conjunction with some spectral dispersion elements such as prisms or other photonic devices.

Means may be provided for doing a principal component analysis. In accordance with the invention, a single modulated measure from a cell consists of multiple, short duration, spectra taken with the excitation laser at different wavelength. All the spectra together form a data set on which a principal component analysis can be performed. Contrary to conventional PCA, the value of the first principal component is not of interest. Instead, it is the associated eigen-spectra, which is the basis vector associated with the first principal component. It is these eigen-spectra (basis-vector) that are then the differential spectra. Here, the PCA is not used to reduce the dimensionality of the data set but to extract the element with the largest variation.

According to the present invention, there is a method for obtaining a Raman spectrum comprising exciting a sample using radiation; capturing light emitted from the sample; modulating the excitation radiation; capturing light emitted in response to the modulated radiation and using the captured radiation to obtain the Raman spectrum. Preferably, the scattered radiation is captured using a multi-channel spectrometer, ideally a CCD camera.

The method may further involve correlating modulations in the excitation radiation with variations in the captured spectra. By doing this, the Raman peak can be more accurately identified, as background fluorescence, for example, should not vary with changes in the excitation signal.

By analysing the light emitted in response to both the initial excitation radiation and its modulated version using PCA, further improvements may be made. This provides a simple technique for pulling out variations in the acquired spectra. If the modulated spectra are fed into a PCA routine, this will look at the variation in the spectra. Because of the modulation, this variation is the moving Raman spectrum only, as the fluorescence remains steady. Thus the PCA routine outputs a spectrum, or principal component that is the differential Raman spectrum of the sample. For the extraction of the differential Raman signal a minimum of one modulation period is necessary.

BRIEF DESCRIPTION OF THE DRAWINGS

Various aspects of the invention will now be described by way of example only and with reference to the accompanying drawings, of which:

FIG. 1 (c) is the resultant Raman spectra from a HL60 cell that is optically trapped in a micro-fluidic channel and exposed to Raman excitation;

DETAILED DESCRIPTION OF THE INVENTION

Figure 1:
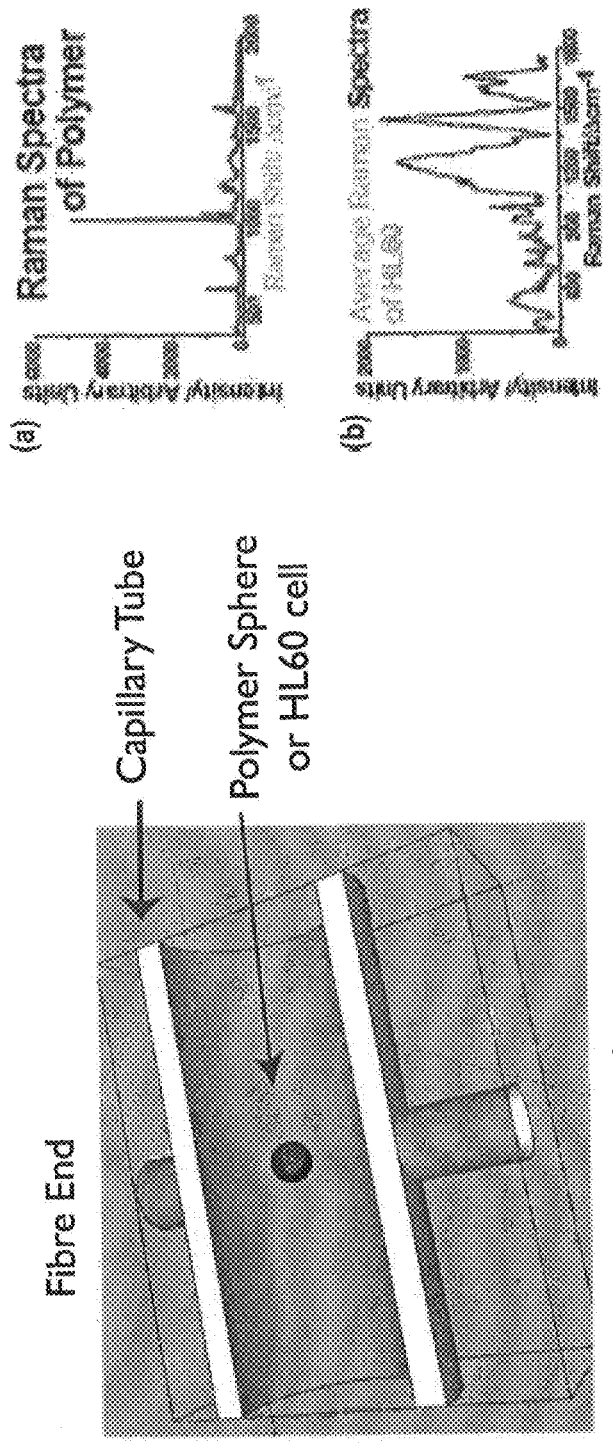
FIG. 1 (a) is an image of a polymer microsphere or HL60 cell that is optically in a micro-fluidic channel and exposed to Raman excitation FIG. 1 (b) is the resultant Raman spectra from a polymer microsphere that is optically trapped in a micro-fluidic channel and exposed to Raman excitation.

FIG. 1(a) shows a microfluidic device that is operable to form an optical trap in a micro-fluidic channel. Any suitable means can be used for causing fluid to flow through the device. The optical trap is formed using two counter propagating diverging beams. In this example, the counter propagating beams are provided via two optical fibres that are positioned on opposing sides of the micro-fluidic channel. In this case, the channel is a micro-capilliary. Radiation is directed via the fibres into the micro-fluidic channel, so that cells or other particles within the fluid can be trapped. Optical traps can be used to allow micrometer-sized particles to be held, moved and generally manipulated without any physical contact. This has been well documented, for example see Ashkin et al Optics Letters Vol. 11, p 288 (1986). Orthogonal to the fibre ends (not shown) is an objective lens for directing a Raman excitation beam onto the cell and capturing the emitted signal so that it can be recorded.

To test the arrangement of FIG. 1(a), a flow system consisting of a capillary, of square cross-section size 80 microns, was connected to a syringe or gravity feed pump. Initially, 10 micron polymer particles were flowed through the capillary tube, and trapped using the counter propagating beams, as and when desired. A 50 mW Raman examination beam was then introduced from below using a Nikon x50 NA 0.9 oil immersion. FIG. 1(b) shows a polymer microsphere trapped inside the capillary, together with the spectra obtained from the sphere. FIG. 1(c) shows a HL60 cell trapped, together with the spectra obtained from this.

By using optical trapping in a microfluidic environment, damage to the particle/cell that is under investigation can be minimised. However, to further reduce this, a statistical approach can be used to allow the Raman signals to be recorded very rapidly from a single cell. This method relies on modulation of the excitation laser, and in particular tuning of the laser wavelength. This can be done using continuous or discontinuous tuning. Statistical analysis of the resultant Raman scatter allows a significant reduction in the time needed to record the signals. This can be done without the addition of foreign particles, such as nanoparticles, specialist surfaces, and/or enhancement schemes.

The physical properties, such as wavelength and intensity, of the Raman excitation vary in time. The resulting Raman signal is then also subject to variations but in a complex way. Indeed, depending on their physical origin the different parts of the Raman spectra behave differently. If the wavelength is modulated then the Raman peaks in the spectra incur a shift in wavelength while the fluorescence background remains constant. In the case of amplitude variation, both peaks and background change in amplitude.

The method of the present invention uses a general wavelength, frequency and amplitude or other parameters variation of the excitation and correlates this with the measured Raman spectra to distinguish between the different components of the spectrum, i.e. background, Raman peaks and noise. The input excitation is encoded with a variation which then is decoded at detection time distinguishing thus between signal, noise and background. Variation of the parameters is used to quantify the correlated variation of the Raman signal.

The encoding method is based on the variation of controlling the parameters of the Raman excitation source such as the laser or any device delivering the necessary excitation output. Examples of these parameters are: laser, diode or device driving current; intra-cavity or external cavity grating position and/or orientation; mechanical or opto-electric change of the cavity length; polarisation variation; excitation mode variation and variation of the optical properties of any intra-cavity or external cavity non-linear optical elements.

Another way to achieve source variation is by using bistable or multi stable lasers that naturally oscillate in a controlled or chaotic fashion between different wavelength and states. Alternatively, two or more laser sources can be combined where each has a different wavelength. Each of the sources can be independently switched and its intensity varied to achieve an efficient modulated multi wavelength excitation.

Figure 2A:
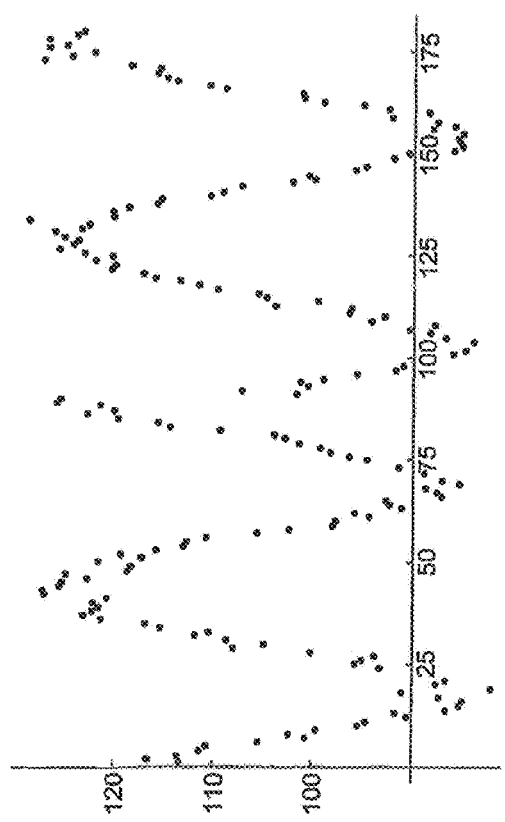
FIG. 2 (a) is a plot of laser intensity as a function of time.
FIG. 2(b) is a plot of laser wavelength as a function of time.
Figure 2B:
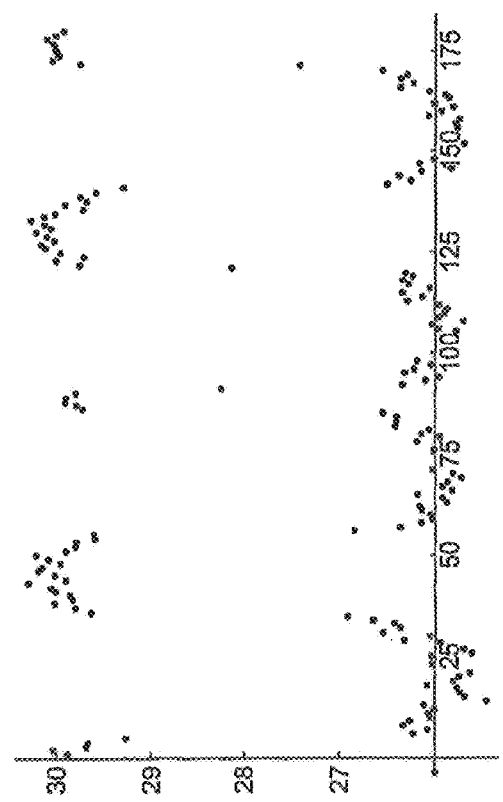

FIG. 2 shows the effect of varying the driving current of the diode laser device. FIG. 2 (a) is a plot of laser intensity as a function of time, and FIG. 2(b) is a plot of laser wavelength as a function of time. As can be seen, varying the drive current induces a wavelength shift and an excitation intensity variation. Because of the non-linear properties of the laser, discrete wavelength jumps occur as the current is varied. These jumps correspond to laser mode hopping.

To obtain the sample response, Raman spectra are repeatedly acquired in as short as possible time slots whose duration is related to the speed of variation of the excitation parameters. Over this duration, the excitation parameters should not vary. For practical reasons, the spectral snapshot can also contain the excitation spectra suitably attenuated in intensity. The excitation spectral information such as wavelength, amplitude and bandwidth can then be retrieved from this snapshot. Alternatively other measures can be used to deduce the excitation characteristics and their variation or the variation can be linked to the control parameters after suitable calibration. Every snapshot is then stored together with the excitation parameters for real-time or successive data treatment.

Figure 3:
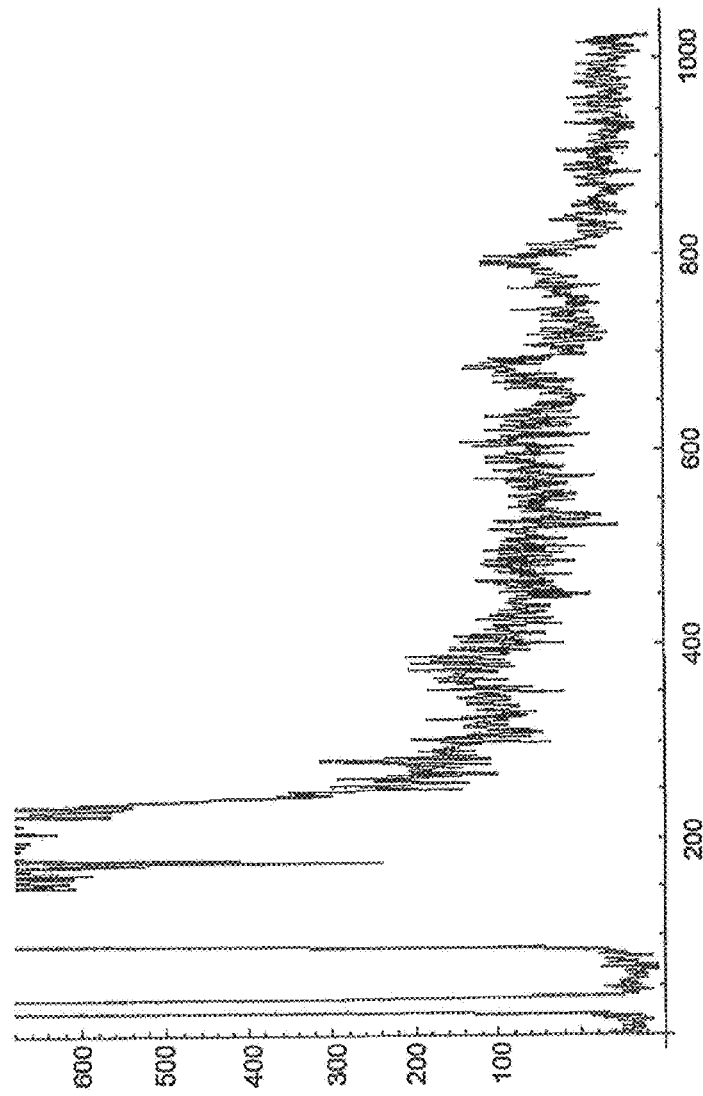
FIG. 3 is a complete Raman spectrum including background, noise, excitation and Raman resonance peaks.

FIG. 3 shows a Raman spectrum that was acquired with duration of 0.5 s. The excitation parameters can be retrieved from the furthest left peak (A), which corresponds to the excitation laser. There are multiple ways to retrieve the Raman peaks from a family of short scans, each taken for different excitation parameters. Some methods cancel directly the background while others do not. A non-exhaustive list of possible methods includes statistical post processing (variance), real time/post processing signal tracking (spectral lock-in amplifier), and real time/post processing leading to differential signal (statistical approach).

Figure 4:
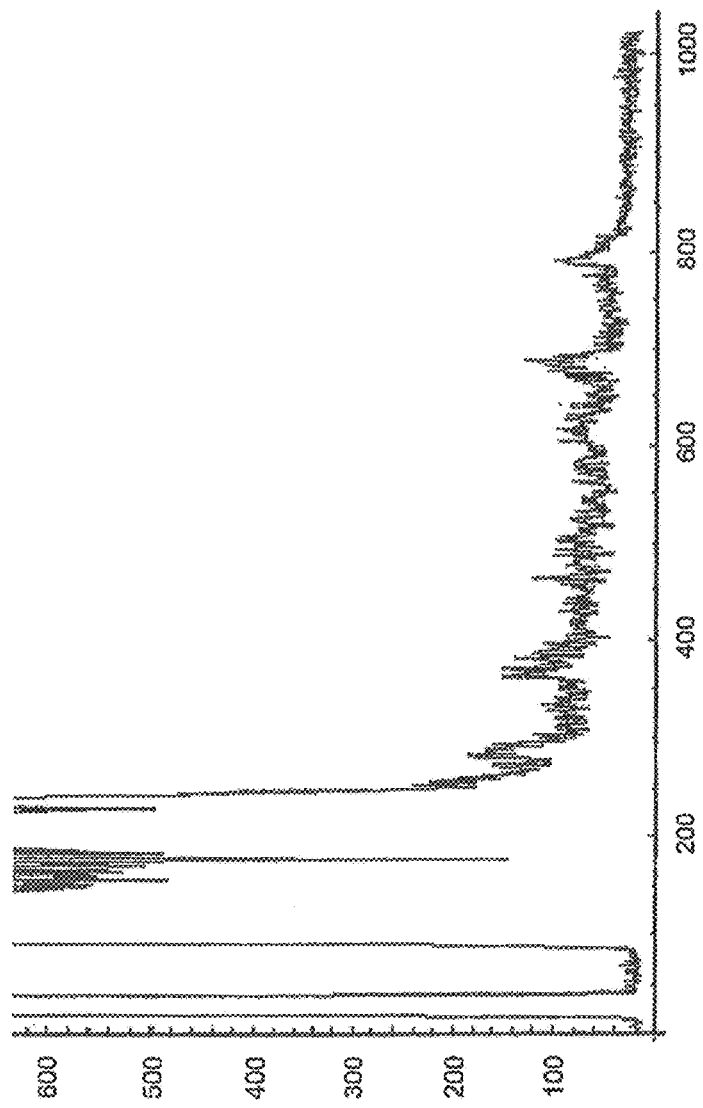
FIG. 4 is a plot of the variance of 90 Raman Spectra of 0.5 s each.

Statistical post processing involves looking at the variation of a family of spectra as a function of wavelength. If the excitation wavelength variation is large enough then the variance of the family of spectra will show different levels of variance for the noise, background and Raman peaks. Indeed the shift of the excitation wavelength implies a shift of the peaks, which is equivalent to a large intensity variation at a given wavelength. The variance of the peak will thus be much higher than the variance of the surrounding region. FIG. 4 shows the resulting Raman spectra after using the statistical post processing method that calculates the variance from 90 Raman spectra of 0.5 s each.

Figure 5:
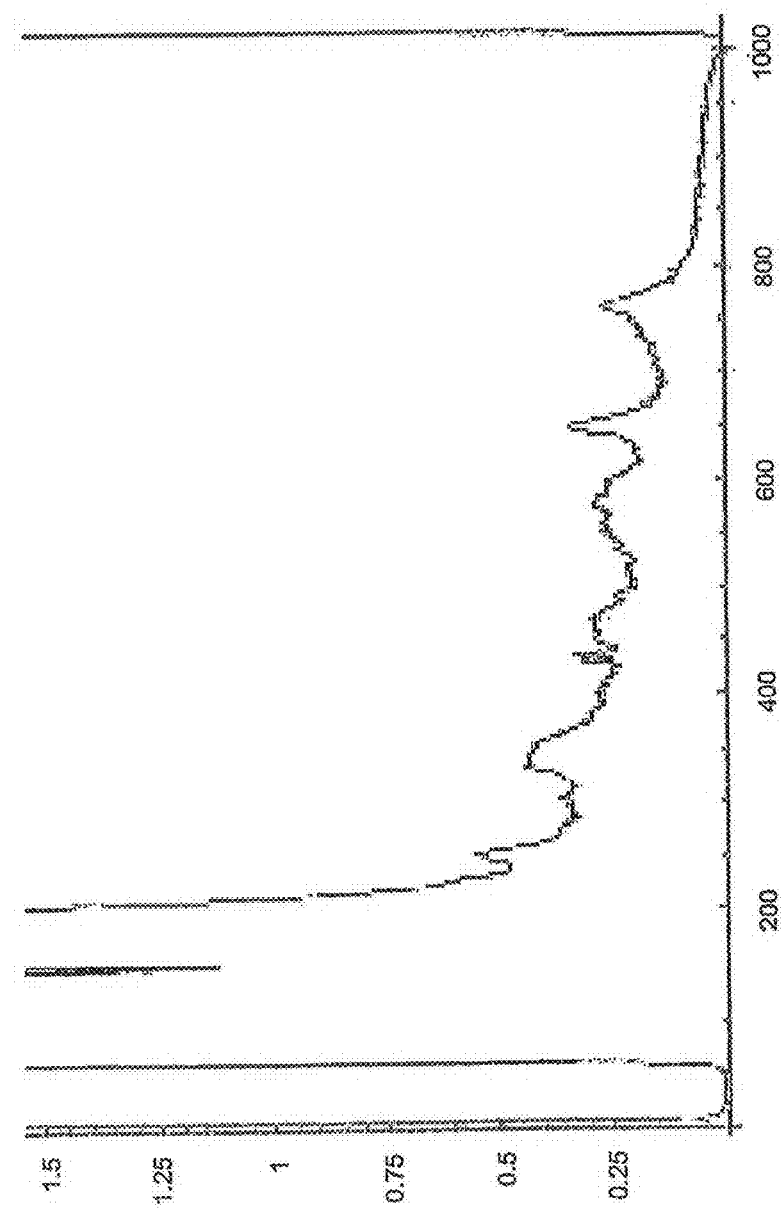
FIG. 5 shows the average Raman spectra using the wavelength tracking and signal renormalisation method.

Real time/post processing signal tracking (spectral lock-in amplifier) involves using the amplitude and wavelength position of the excitation laser peak to shift and normalise the individual 0.5 s Raman spectra before averaging them. However, this method does not cancel the background and is disadvantaged by the laser mode hopping. It is similar to a lock-in amplifier as it locks-in onto the reference excitation wavelength and uses its shift to reconstruct the resonances. FIG. 5 shows the processed Raman spectra using the excitation wavelength and amplitude tracking method.

Figure 6A:
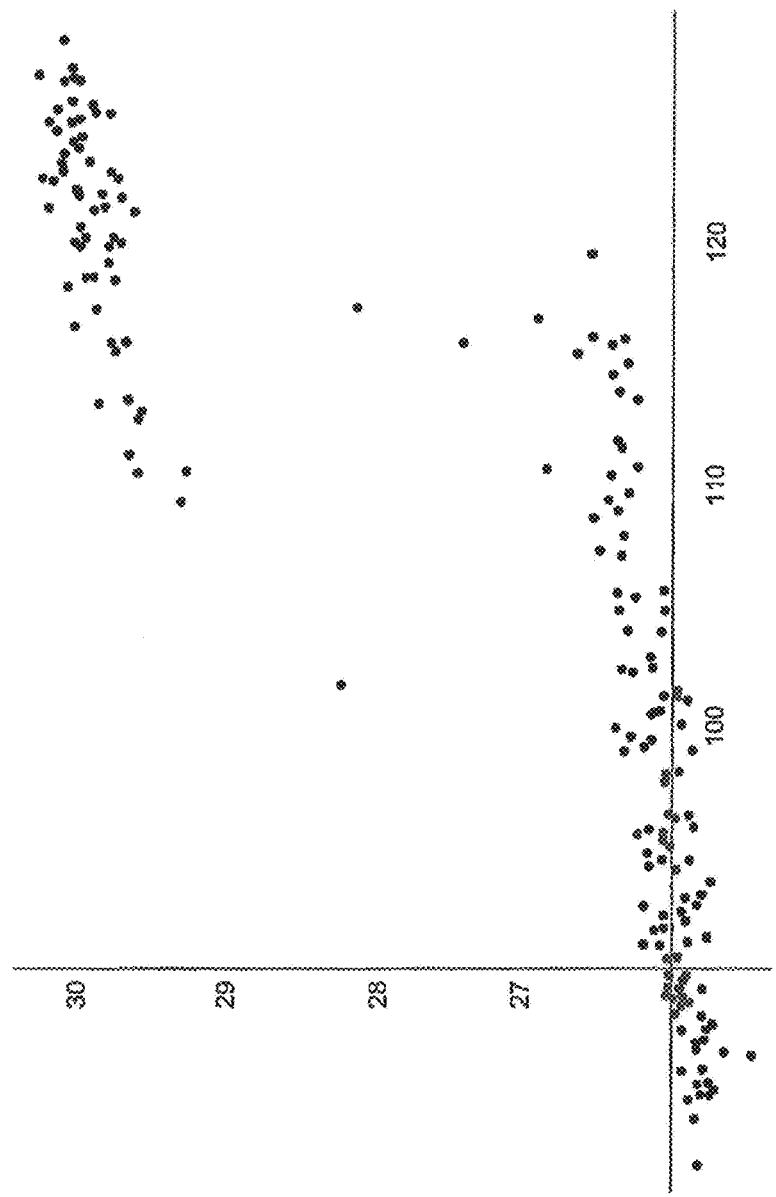
FIG. 6(a) is a plot of wavenumber versus intensity of the laser.
Figure 6B:
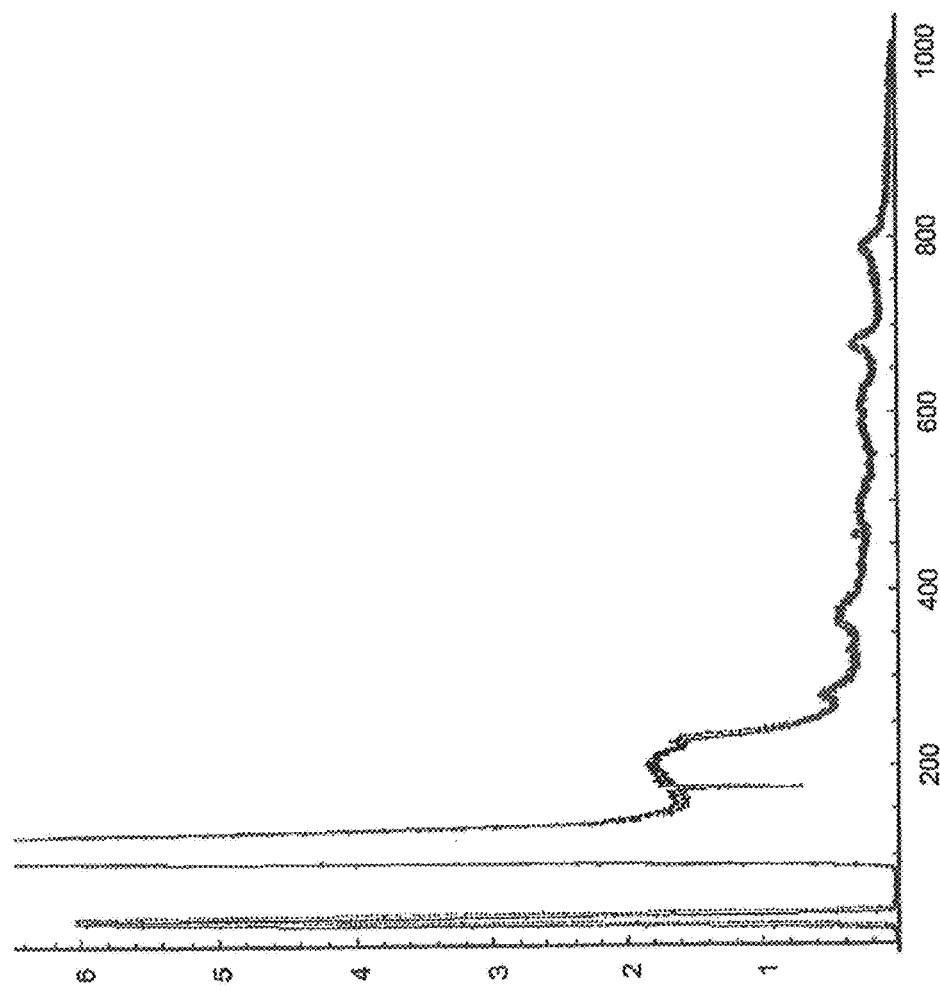
FIG. 6(b) is a plot of binned and averaged spectra.
Figure 7:
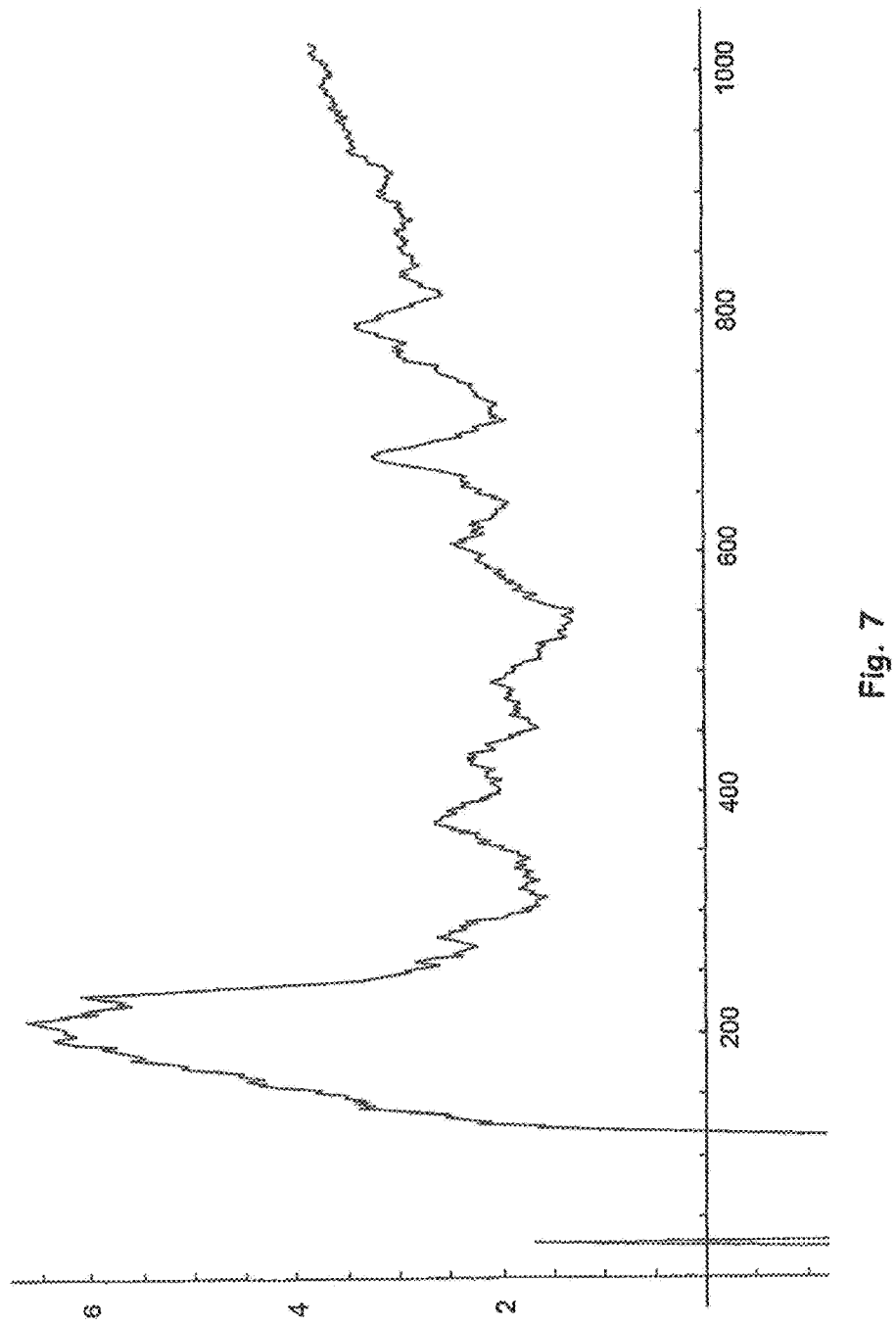
FIG. 7 is a plot of integrated differential Raman signal as a function wavelength.
Figure 8:
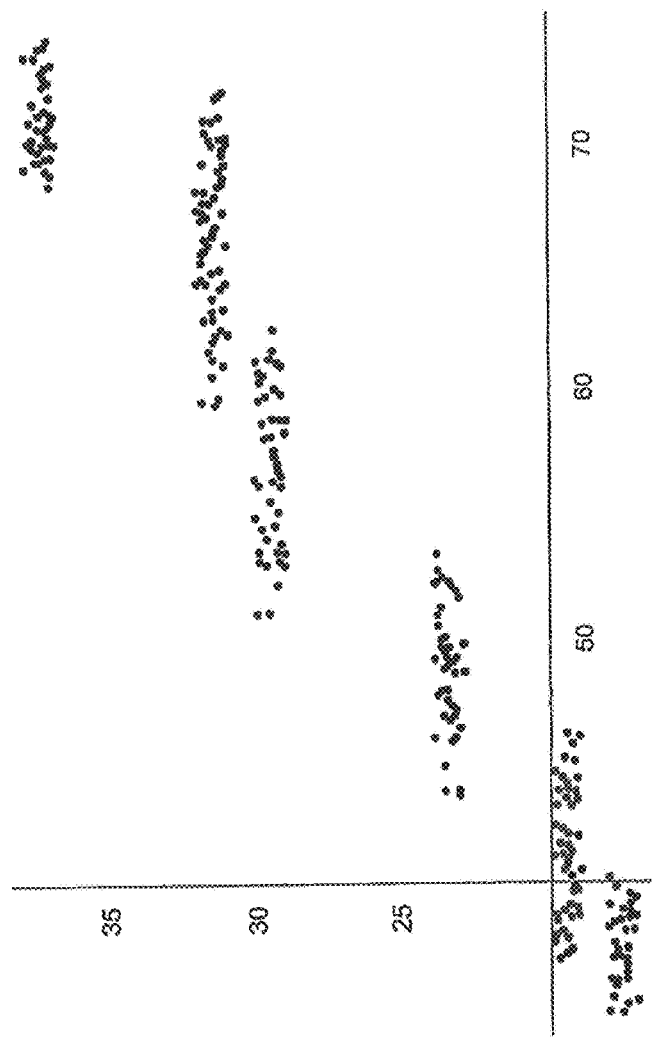
FIG. 8 is plot of simulated wavelength versus intensity in a multi-stable lasing device.

Real time/Post processing leading to differential signal (statistical approach) involves using a differential signal to eliminate the background. This can be achieved by using two laser states with different wavelengths. When plotting the amplitude versus the wavelength of the excitation laser while the driving currant is varied the number of modes accessed by the parameter variation can be recognised, as shown in FIG. 6(a), which is a plot of wavenumber versus intensity of the laser, and FIG. 6(b), which is a plot of binned and averaged spectra. In this case, the wavelength position of the laser peak is used to average only spectra where the excitation laser has a specific wavelength. The spectra in a bin are normalised with the amplitude of the laser intensity and then averaged. Because of the bi-stability there are only two bins. The differential signal corresponds in this case to the difference between the red and blue curve. When calculating this difference the background part of the signal is removed. The difference can then be integrated to retrieve original Raman resonance peaks, as shown in FIG. 7. This method can be generalised to multi stable lasing devices. FIG. 8 shows a simulated wavelength versus intensity in a multi-stable lasing device. In this multiple stabilities will increase the differential signal as this can be calculated using n-point differential formulas.

Figure 9:
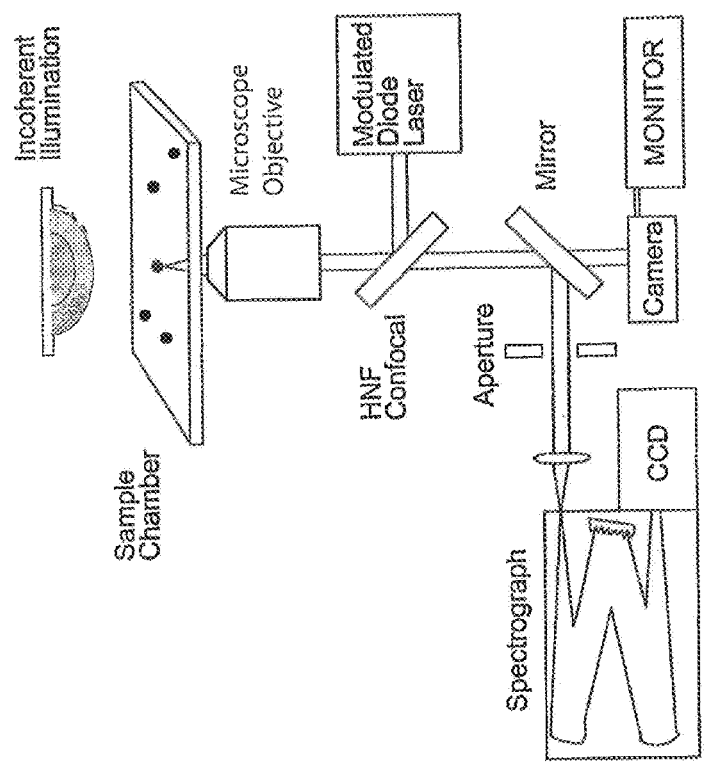
FIG. 9 is a diagram of an alternative optical arrangement for trapping a single cell and obtaining Raman spectra from it.

FIG. 9 shows a more detailed system for providing a modulated Raman excitation signal in accordance with the invention. This has a laser that can be modulated in some form: mechanically, optically or by current. This is then reflected against a holographic notch filter that reflects a very narrow band around the wavelength and transmits all other wavelengths, into a microscope objective that focuses the beam to the sample. The Raman signal is collected by the same microscope objective and transmitted through the notch filter onto a dichroic mirror, which reflects the infrared Raman scatter whilst allowing the visible incoherent light, which illuminates the sample, to pass to a viewing camera. This allows an image of the sample under study to be collected as well as its Raman spectrum. The collected Raman scatter is then passed through an optional confocal aperture to reject any unwanted signal surrounding the sample of interest. The signal is finally imaged onto a 550 mm spectrograph equipped with a 300 lines/mm grating to separate spatially all the collected Raman wavelengths that are imaged onto a multi-channel detector, for example a CCD camera. The CCD camera is a liquid nitrogen cooled CCD that has a pixel array of 2048×512 with each pixel measuring 13.5 µm square, the array having a bandwidth of one pixel, i.e. about 0.15 nm. The combined resolution of the spectrograph is 0.078 nm allowing the movement of the laser and hence Raman spectrum to be captured.

Figure 10:
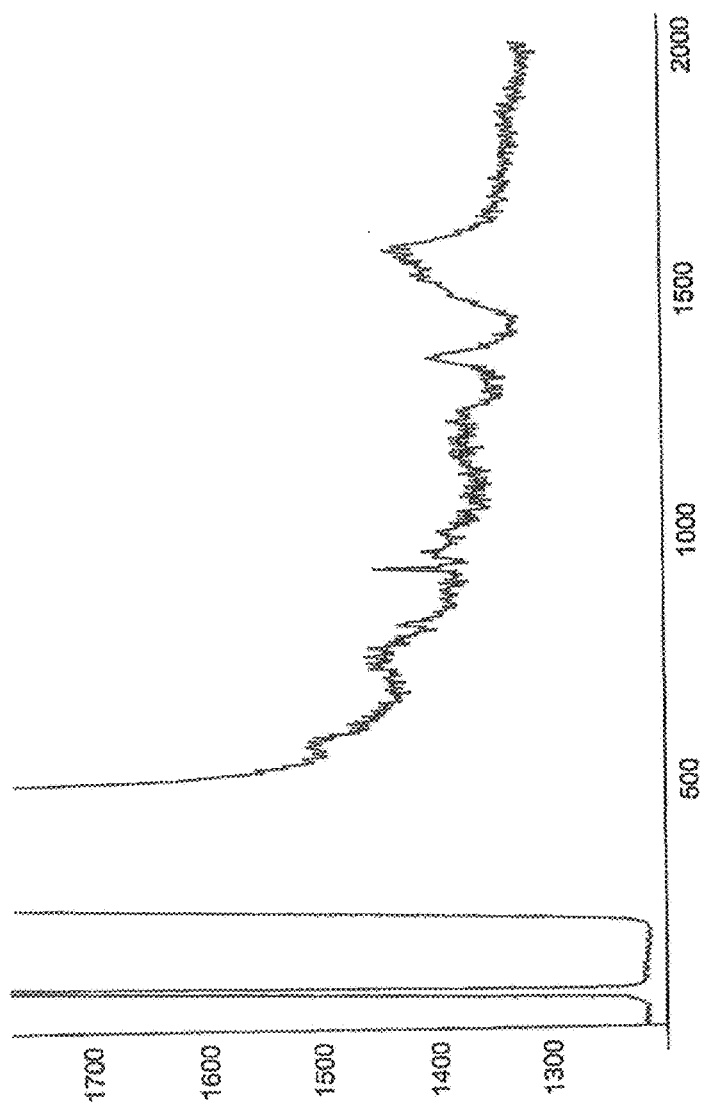
FIG. 10 is a single Raman spectrum recorded at one wavelength.
Figure 11:
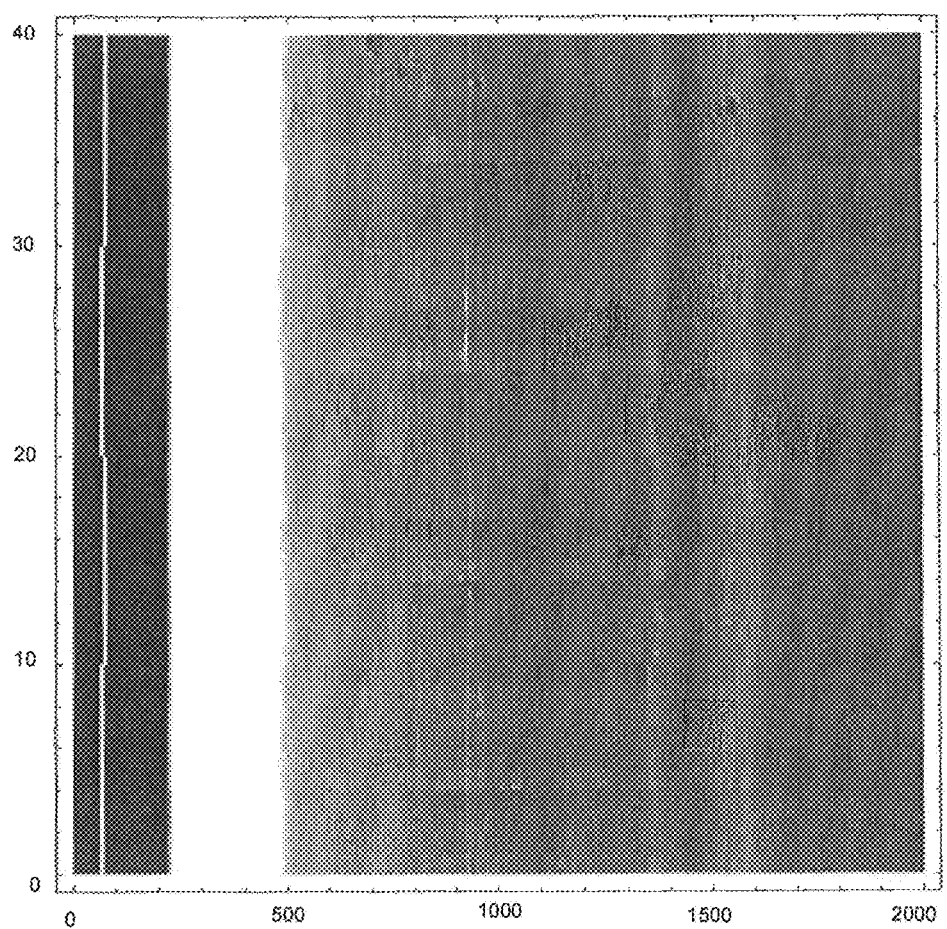
FIG. 11 is a sequential recording of the Raman signal as the laser, and hence Raman spectra, was modulated between two fixed wavelengths.
Figure 12:
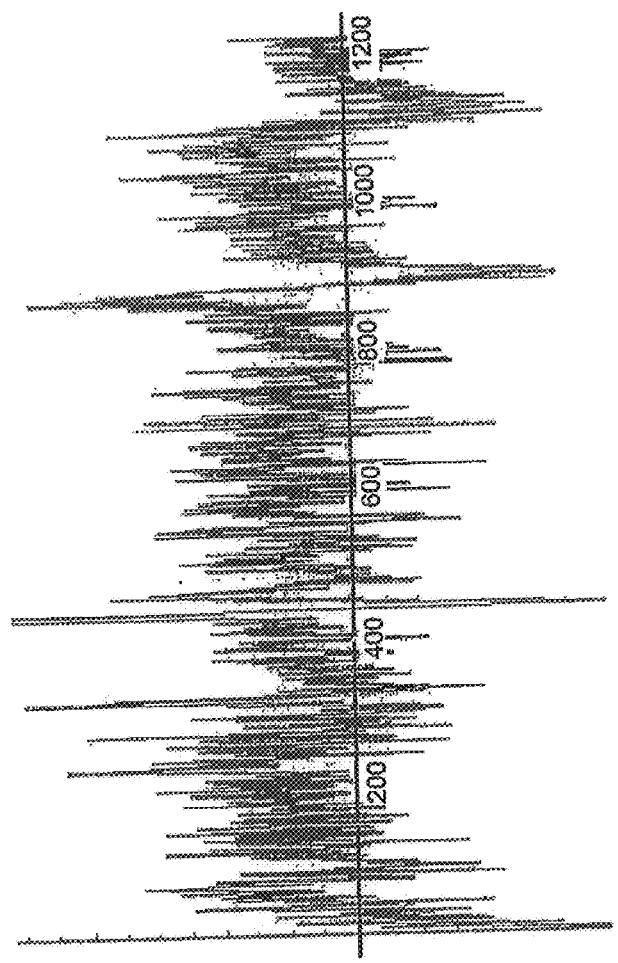
FIG. 12 is a plot of a differential Raman spectrum of a cell extracted from the modulated Raman signal.

In order to remove or reduce fluorescence in the acquired Raman spectra, as well as reduce the acquisition times the excitation wavelength is modulated and multiple spectra collected. The Raman spectra are then extracted from these multiple spectra. To improve extraction of the Raman spectrum from the modulated data, an external cavity laser diode was used in a Littman-Metcalf configuration. This configuration allows a significantly greater tuning range (~30 nm) compared to the bandwidth of one pixel (0.15 nm) of the detecting CCD mounted on the spectrometer, improving the detection of the modulation significantly. This laser was used to switch between two wavelength positions that in turn modulated the Raman spectra between two positions. A signal was acquired at each wavelength position as it was moved between the two wavelengths. A single spectrum can be seen in FIG. 10, which shows single spectrum recorded at one wavelength position. Multiple signals were acquired at each wavelength position as it was modulated. FIG. 11 shows the sequential recording of the Raman spectra as the laser was modulated between two fixed wavelengths. The jumps in the spectra can be clearly seen. The laser is on the extreme left and the Raman peaks to the right of this.

To improve the detection of variations in the acquired spectra a modified version of conventional PCA can be used. This pulls out variation in the acquired spectra. If the modulated spectra are fed into a PCA routine, this will look at the variation in the spectra. Because of the modulation, this variation is the moving Raman spectrum only, as the fluorescence remains steady. Thus the PCA routine outputs a spectrum, or principal component that is the differential Raman spectrum of the sample. For the extraction of the differential Raman signal a minimum of one modulation period is necessary.

FIG. 11 shows an example of a differential spectrum after PCA processing. This differential spectrum can be integrated to reproduce the normal Raman spectrum of the sample or left as is for further statistical analysis. An advantage of using PCA in this way is that the output is the variation in the Raman spectrum. Thus, there is no need to track the laser line allowing points of interest in the spectra to be identified and giving much more flexibility in the choice of instrumentation such as which grating to use. This method also removes the fluorescence background. It should be noted that fluorescence is not always a problem in viewing the spectrum, but is more of a problem in subsequent statistical analysis where it can severely affect the efficiency of discrimination between two sample sets such as healthy and diseased cells.

In order to evaluate the ability of this technique to effectively remove fluorescence and potentially reduce acquisition times a comparison was made with conventional PCA Raman processing and the combined modulation/PCA processing of the invention. This was done for sets of Raman spectra acquired from different regions in a biological cell, nucleus and cytoplasm. Ten Raman spectra were collected from the nucleus and cytoplasm. The spectra were acquired in two minutes for both conventional PCA Raman processing and the combined modulation/PCA processing of the invention. To test the acquisition time reducing potential of the invention spectra for the modulated/PCA were also acquired in one minute.

Figure 13:
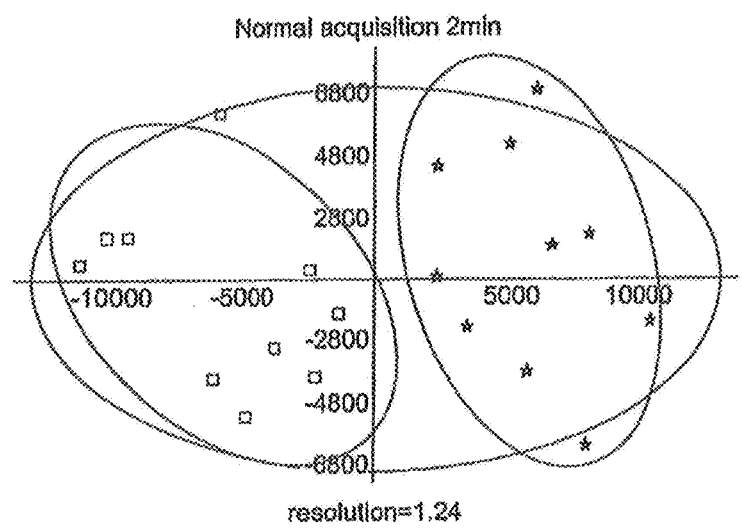
FIG. 13 shows the results of a PCA analysis carried out to compare the effect of acquiring a Raman signal using conventional processes and a process in accordance with the invention.
Figure 13:
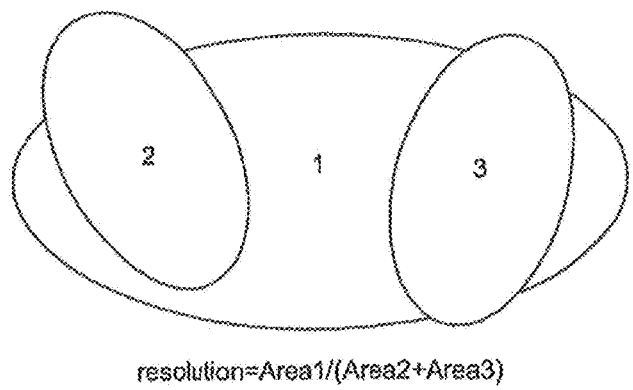
Figure 13:
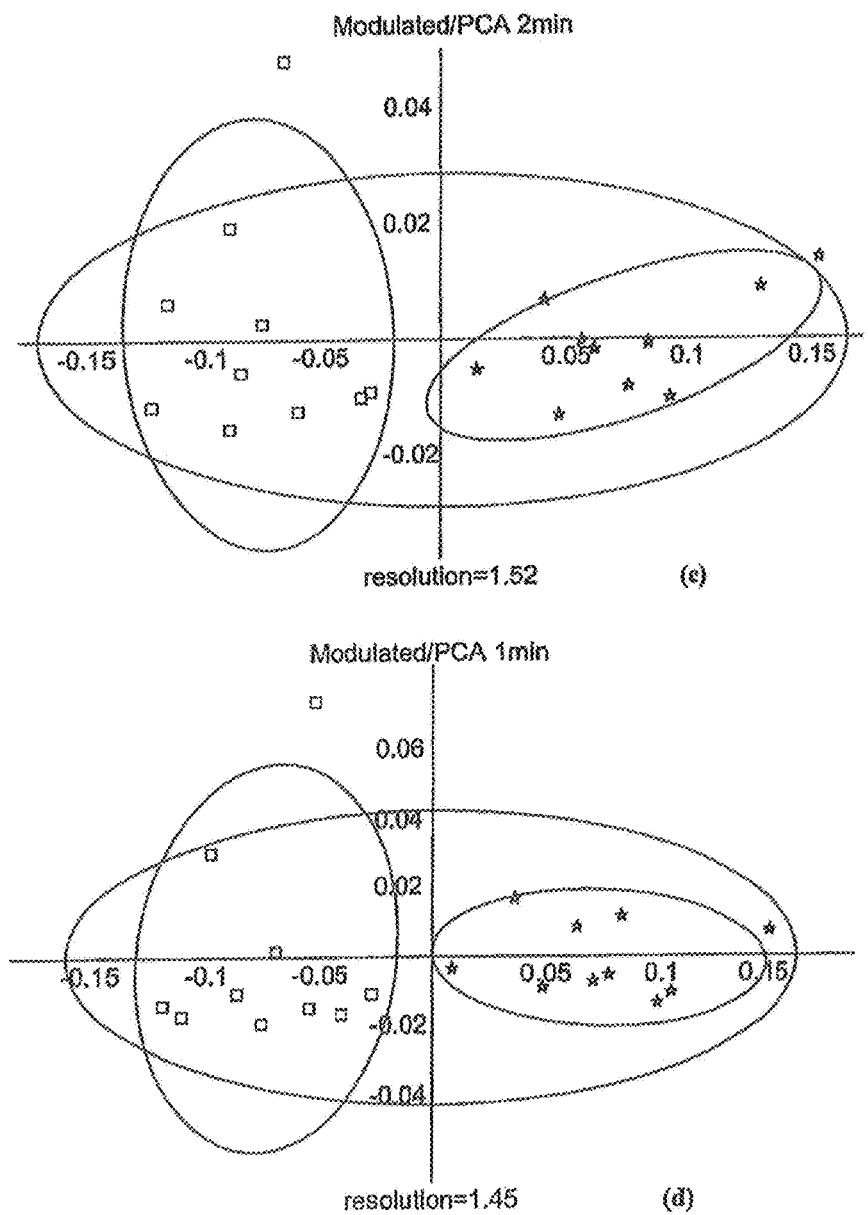

FIG. 13 shows the results of the PCA analysis carried out to compare the effect of acquiring the signal nommally to the modulated/PCA method of acquiring the Raman signal. FIG. 13(a) shows the diagrammatic definition of the resolution used in FIGS. 13(b) to 13(a). From FIGS. 13(b) and (c), it can be seen that the resolution greatly increases when the Raman signal is acquired using the modulated/PCA method. This is because it removes the fluorescence that has a negative impact on the diagnostic PCA model. This may be important in medical diagnostics as patient-to-patient variability in fluorescence may greatly affect any diagnostic models based on Raman spectroscopy. Furthermore, as shown in FIG. 13(d) and FIG. 13(e) even when the acquisition time is halved, the modulated/PCA Raman spectra provides a much better resolution compared to the discrimination based on the normal acquisition indicating that the acquisition time could be reduced by a factor of at least two.

The present invention provides a system that allows single cells to be optically trapped and held, and Raman signals to be acquired from these cells in a very short time. Contrary to 1978 paper, where the Raman signal was acquired with a slowly scanning single channel detection system (2.4 nm/min), the present invention combines the advantages of acquiring the modulated Raman signals with modern multi-channel CCD detection allowing a rapid acquisition whilst excluding the fluorescence background. Additionally, the invention improves subsequent statistical analyses such as Principal Component Analysis (PCA) important medical diagnostics for example. Using excitation signal modulation, signals can be acquired in ~1/10 to 1/50 of the time that would normally be required. This means that damage to cells due to over exposure to the Raman excitation can be minimised.

A skilled person will appreciate that variations of the disclosed arrangements are possible without departing from the invention. For example, whilst a micro-capilliary is described in other embodiments, the microfluidic flow may be implemented using channels made using soft lithography in PDMS or similar and the size of the channel may naturally vary. Accordingly the above description of the specific embodiment is made by way of example only and not for the purposes of limitation. It will be clear to the skilled person that minor modifications may be made without significant changes to the operation described.

The invention claimed is:

1. A system comprising means for optically trapping a particle and a radiation source for causing Raman scatter from the particle whilst in the optical trap, wherein the means for forming an optical trap comprise a dual beam arrangement, in which counter propagating optical beams are used to hold the particle, and wherein the source emits radiation orthogonal to the trapping beams, wherein the radiation source comprises two or more laser sources each independently switchable and operable to vary its intensity between multiple levels, each of the multiple levels of intensity being sufficient to cause Raman scatter, thereby to achieve intensity modulated multi wavelength excitation.

2. A system as claimed in claim 1 comprising modulating means for modulating the radiation emitted from the two or more laser sources.

3. A system as claimed in claim 2 wherein the modulating means is operable to encode information onto one or more parameters of the excitation signal.

4. A system as claimed in claim 2, wherein said modulating means is operable to modulate one or more of the following: excitation laser wavelength; excitation laser driving current; intra-cavity or external cavity grating position and/or orientation; laser cavity length; excitation laser polarization; excitation mode and optical properties of any intra-cavity or external cavity non-linear optical elements.

5. A system as claimed in claim 1 wherein the two or more laser sources each comprise a laser diode.

6. A system as claimed in claim 5 wherein the two or more laser diodes are in a Littrow or Littman-Metcalf configuration.

7. A system comprising means for optically trapping a particle and a radiation source for causing Raman scatter from the particle whilst in the optical trap, wherein the radiation source comprises two or more laser sources each operable to output a different wavelength, and wherein each of the sources is independently switchable and operable to vary its intensity between multiple levels, each of the multiple levels of intensity being sufficient to cause Raman scatter, thereby to achieve intensity modulated multi wavelength excitation.

8. A system as claimed in claim 1 comprising a detector for capturing the scattered light.

9. A system as claimed in claim 8 wherein the detector is a multi-channel spectrometer.

10. A method for obtaining a Raman spectrum comprising:
exciting a sample or particle using radiation from two or more laser sources that are operable to output a different wavelength and are independently switchable and operable to vary intensity between multiple levels of intensity, each of the multiple levels of intensity being sufficient to cause Raman scatter, thereby to achieve intensity modulated multi-wavelength excitation;
capturing light scattered from the sample or particle using a multi-channel spectrometer comprising a CCD camera;
modulating the excitation radiation;
exciting the sample or particle using the modulated radiation;
capturing scattered radiation associated with the modulated radiation; and
identifying variations in the captured radiation associated with the modulation, thereby to obtain a Raman spectrum or a function thereof for the sample or particle.

11. A method as claimed in claim 10 comprising modulating one or more of the following:
excitation wavelength;
excitation laser driving current;
intra-cavity or external cavity grating position and/or orientation;
laser cavity length;
excitation laser polarization; and
excitation mode and optical properties of any intra-cavity or external cavity non-linear optical elements.

12. A method as claimed in claim 11 comprising modulating the excitation wavelength by switching between two or more different wavelengths.

13. A method as claimed in claim 10 comprising applying primary component analysis to the captured light.

14. A system as claimed in claim 7 comprising modulating means for modulating radiation emitted from the two or more laser sources.

15. A system as claimed in claim 14 wherein the modulating means is operable to encode information onto one or more parameters of the excitation signal.

16. A system as claimed in claim 14, wherein said modulating means is operable to modulate one or more of the following:
excitation laser wavelength;
excitation laser driving current;
intra-cavity or external cavity grating position and/or orientation;
laser cavity length;
excitation laser polarization; and
excitation mode and optical properties of any intra-cavity or external cavity non-linear optical elements.

17. A system as claimed in claim 7 wherein the two or more laser sources each comprise a laser diode.

18. A system as claimed in claim 17 wherein the two or more laser diodes are in a Littrow or Littman-Metcalf configuration.

19. A system as claimed in claim 1 wherein the system is a micro-fluidic system.

20. A system as claimed in claim 7 wherein the system is a micro-fluidic system.

* * * * *